United States Patent
Kucera et al.

(10) Patent No.: US 9,499,811 B2
(45) Date of Patent: *Nov. 22, 2016

(54) LIGATION ENHANCEMENT

(71) Applicant: New England Biolabs, Inc., Ipswich, MA (US)

(72) Inventors: Rebecca Kucera, Hamilton, MA (US); Thomas C. Evans, Jr., Topsfield, MA (US)

(73) Assignee: New England Biolabs, Inc., Ipswich, MA (US)

( * ) Notice: Subject to any disclaimer, the term of this patent is extended or adjusted under 35 U.S.C. 154(b) by 242 days.

This patent is subject to a terminal disclaimer.

(21) Appl. No.: 14/190,747

(22) Filed: Feb. 26, 2014

(65) Prior Publication Data

US 2014/0187447 A1   Jul. 3, 2014

Related U.S. Application Data

(63) Continuation of application No. 13/464,548, filed on May 4, 2012, now Pat. No. 8,697,408.

(60) Provisional application No. 61/483,348, filed on May 6, 2011.

(51) Int. Cl.
| | |
|---|---|
| *C12N 15/10* | (2006.01) |
| *C12N 9/00* | (2006.01) |
| *C12P 19/34* | (2006.01) |
| *C12Q 1/68* | (2006.01) |

(52) U.S. Cl.
CPC ............. *C12N 15/10* (2013.01); *C12N 9/93* (2013.01); *C12P 19/34* (2013.01); *C12Q 1/6832* (2013.01); *Y02P 20/52* (2015.11)

(58) Field of Classification Search
None
See application file for complete search history.

(56) References Cited

U.S. PATENT DOCUMENTS

2007/0054272 A1*  3/2007  Brachet et al. ...... C12Q 1/6855
                                                           435/6.12

OTHER PUBLICATIONS

Takahashi et al., "Thermophilic HB8 DNA Ligase: Effects of Polyethylene Glycols and Polyamines on Blunt-End Ligation of DNA," J. Biochem. 1986, 100:123-131.*
Aravin A, et al. FEBS Lett. 579(26):5830-40 (2005).
Edwards et al. Nucleic Acids Research 19(19):5227-32 (1991).
Hayashi et al. Nucleic Acids Research 14(19): 7617-7630 (1986).
Pheiffer and Zimmerman Nucleic Acids Research 11(22):7853-71 (1983).
Xiao et al. Molecular Biotechnology 35(2):129-133 (2007).

* cited by examiner

*Primary Examiner* — Kaijiang Zhang
(74) *Attorney, Agent, or Firm* — New England Biolabs, Inc; Harriet M. Strimpel

(57) ABSTRACT

Compositions and methods are provided for enhancing enzymatic ligation between nucleic acid fragments that relies on one or more small molecule enhancers having a size of less than 1000 daltons. For example, enhancement of ligation efficiencies are observed for double-stranded nucleic acid fragments that are blunt-ended, have a single nucleotide overhang at the ligation end, or have staggered ends compared to ligation under similar conditions in the absence of the one or more small molecule ligation enhancer. The use of small molecule enhancers for ligating nucleic acids results in an increased number of transformed host cells after transformation with the ligated molecules. This enhancement can be observed with chemically transformed host cells and with host cells transformed by electroporation.

6 Claims, 6 Drawing Sheets

SEQUENCE LISTING

```
<160> NUMBER OF SEQ ID NOS: 4

<210> SEQ ID NO 1
<211> LENGTH: 11
<212> TYPE: DNA
<213> ORGANISM: unknown
<220> FEATURE:
<223> OTHER INFORMATION: AhdI recognition site of top strand and bottom
      strand of DNA: can exist in many organisms
<220> FEATURE:
<221> NAME/KEY: misc_feature
<222> LOCATION: (4)..(8)
<223> OTHER INFORMATION: n is a, c, g, or t

<400> SEQUENCE: 1
gacnnnnngt c                                                          11
```

```
<210> SEQ ID NO 2
<211> LENGTH: 12
<212> TYPE: DNA
<213> ORGANISM: unknown
<220> FEATURE:
<223> OTHER INFORMATION: recognition site of top strand of DNA for
      BciVI: can exist in many organisms
<220> FEATURE:
<221> NAME/KEY: misc_feature
<222> LOCATION: (7)..(12)
<223> OTHER INFORMATION: n is a, c, g, or t

<400> SEQUENCE: 2
gtatccnnnn nn                                                          12

<210> SEQ ID NO 3
<211> LENGTH: 11
<212> TYPE: DNA
<213> ORGANISM: unknown
<220> FEATURE:
<223> OTHER INFORMATION: recognition site of bottom strand of DNA for
      BciVI: can exist in many organisms
<220> FEATURE:
<221> NAME/KEY: misc_feature
<222> LOCATION: (1)..(5)
<223> OTHER INFORMATION: n is a, c, g, or t

<400> SEQUENCE: 3
nnnnnggata c                                                           11

<210> SEQ ID NO 4
<211> LENGTH: 10
<212> TYPE: DNA
<213> ORGANISM: unknown
<220> FEATURE:
<223> OTHER INFORMATION: recognition site of bottom strand of DNA for
      BccI: can exist in many organisms
<220> FEATURE:
<221> NAME/KEY: misc_feature
<222> LOCATION: (1)..(5)
<223> OTHER INFORMATION: n is a, c, g, or t

<400> SEQUENCE: 4 nnnnngatgg                                                             10
```

LIGATION ENHANCEMENT

CROSS REFERENCE

This application is a continuation of U.S. patent application Ser. No. 13/464,548, filed May 4, 2012 now U.S. Pat. No. 8,697,408, which claims right of priority to U.S. Provisional Application No. 61/483,348 filed May 6, 2011, all of which are incorporated by reference herein in their entirety.

BACKGROUND

Double-stranded nucleic acids containing staggered ends, blunt ends or terminal overhangs of one or two bases can be joined by means of intermolecular or intramolecular ligation reactions. However, ligation of polynucleotides with blunt ends or with one or two base overhangs has been found to be very inefficient. It has been reported that polyethylene glycol (PEG) 6000 can enhance ligation of blunt-ended double-stranded polynucleotides but this reagent interferes with subsequent electroporation of competent cells, a common step in cloning and library preparation.

Using restriction endonuclease-cleaved DNA to create staggered ends, Hayashi et al. (*Nucleic Acids Research* 14(19):7617-7630 (1986)) ligated double-stranded DNA with a four-base overhang using T4 DNA ligase and 6%-10% (w/v) PEG 6000 to enhance intramolecular ligation and 10% PEG 6000 containing divalent cations or polyamines to enhance intermolecular ligation. Pheiffer et al. (*Nucleic Acids Research* 11(22):7853-71 (1983)) reported that polymers such as PEG, bovine serum albumen or glycogen could stimulate blunt-end ligation generated by restriction endonuclease cleavage using T4 DNA ligase. In this reference, the authors reported that smaller molecules PEG 200 or PEG 400 had little effect on ligation. Xiao et al. (*Molecular Biotechnology* 35: 129-133 (2007)) investigated the effects of the organic compounds dimethyl sulfoxide (DMSO), Tween®-20 (Uniqema America LLC, Wilmington, Del.), glycerol, formamide and PEG 6000 on the efficiency and specificity of ligase-detection reactions. They reported that all these compounds except PEG 6000 inhibited the efficiency of ligation although at low concentrations (0-1%) there was a boost in efficiency using Tween-20 which then decreased dramatically. DMSO, glycerol and formamide inhibited the efficiency of the ligation reaction at nick junctions in double-stranded DNA.

Blunt-ended or staggered-ended double-stranded polynucleotides are commonly the product of restriction endonuclease-digestion or fragmentation and polishing. Double-stranded polynucleotides with a single-base overhang are commonly products of PCR amplification using non-proofreading polymerases or the product of adding a dA to a blunt-ended fragment. Alternatively, polishing of the single-base overhang can result in a blunt end. Intermolecular ligation of a restriction endonuclease-cleaved polynucleotide or PCR-amplified polynucleotide to a vector is commonly required prior to a cloning step involving transformation of competent cells.

Intermolecular ligation of single-stranded polynucleotides is undertaken in methods which, for example, involve the ligation of barcode sequences to single-stranded polynucleotides such as cDNA or RNA for cDNA libraries (Edwards et al. *Nucleic Acids Research* 19(19):5227-32 (1991)) or microRNA cloning (Aravin A, et al. *FEBS Lett.* 579(26):5830-40 (2005). Epub 2005)) or for sequencing or multi-array techniques. It would be desirable to improve the efficiency of intermolecular and intramolecular ligations of single-stranded and double-stranded polynucleotides without inhibiting downstream reactions.

SUMMARY

In general in a first aspect, a composition includes a ligase and one or more small molecule ligation enhancers having a molecular weight of less than 1000 daltons.

Various embodiments include one or more of the following features:

- a ligase reaction buffer contains a small molecule enhancer having a concentration of 1%-50% v/v that is capable of enhancing, by at least 25%, intramolecular or intermolecular ligation of a polynucleotide fragment or fragments than would otherwise be obtained in the absence of the enhancer;
- the one or more small molecule ligation enhancers are selected from an optionally substituted straight or branched chain diol or polyol containing 2 to 20 carbons, alcohols, zwitterionic compounds and polar aprotic molecules;
- the optionally substituted straight or branched diol or polyol is selected from the group consisting of 1,2-ethylene glycol, 1,2-propanediol (1,2-PrD), 1,3-propanediol (1,3-PrD), glycerol, pentaerythritol, sorbitol, diethylene glycol, dipropyleneglycol, neopentyl glycol, 2-methyl-1,3-propanediol, 2,2-dimethy-1,3-propanediol, 1,3-butanediol, and 1,4-butanediol 1,5-pentanediol, 1,6-hexanediol, 1,9-nonanediol, 1,12-dodecanediol, 2,2'-dimethylpropylene glycol, 1,3-butylethylpropanediol, methylpropanediol, methylpentanediols, propylene glycol methyl ether, dipropylene glycol methyl ether, tripropylene glycol methyl ether, propylene glycol isobutyl ether, ethylene glycol methyl ether, ethylene glycol ethyl ether, ethylene glycol butyl ether, diethylene glycol phenyl ether, and propylene glycol phenol ether;
- the alcohol is an optionally substituted straight or branched aliphatic primary, secondary, tertiary alcohol chain alkylene group or polyvalent branched chain alkyl group, containing from 2 to 20 carbons;
- the zwitterionic compound is optionally substituted, straight or branched, containing from 2 to 50 carbons and further includes an ammonium, phosphonium, or sulphonium cationic group, a carboxylate, phosphate or sulfate anionic group;
- the polar aprotic molecule is selected from the group consisting of N-alkylcaprolactams, dimethylcaprylic/capric amides, N-alkylpyrrolidones, diphenyl sulfone, DMSO, N,N'-dimethyl imidazolidin-2-one (DMI), acetonitrile, acetone, diglyme, tetraglyme, tetrahydrofuran (THF), dimethylacetamide, and dimethylformamide (DMF);
- the one or more small molecule enhancers comprise a propylene glycol and an ethylene glycol ether;
- the one or more small molecule enhancers are selected from the group consisting of: 1,2-ethylene glycol, 1,2-PrD, 1,3-PrD, isopropyl alcohol, 1,4-butanediol, 1,5-pentanediol, 1,6-hexanediol;
- the small molecule enhancer is selected from the group consisting of: a quaternary ammonium or phosphonium cation and a carboxylate anion;
- the small molecule enhancer is selected from the group consisting of: 1,2-PrD, 1,3-PrD, ethylene glycol, ethanol, isopropanol, and betaine;
- the small molecule enhancer is DMSO;

the small molecule enhancer is 1,2-PrD;

the composition further includes PEG;

the amount of the small molecule enhancer is in the range of 2%-20% v/v;

at least two nucleic acid fragments wherein the nucleic acid fragments are double-stranded DNA having blunt ends for ligation to each other and the ligase is a DNA ligase;

at least two nucleic acid fragments where the nucleic acid fragments are double-stranded DNA having single-base overhangs for ligation to each other; and the ligase is a DNA ligase; and/or the DNA ligase is selected from the group consisting of T3 DNA ligase, T4 DNA ligase, T7 DNA ligase, Taq Ligase, Ampligase®, E. coli ligase and a Sso7-ligase fusion.

In general in a second aspect, a reaction mixture is provided that includes a ligase, one or more small molecule ligation enhancers, and a ligation buffer in the absence of PEG.

In general in a third aspect, a method is provided of enhancing ligation between nucleic acid fragments, the method including: mixing a small molecule ligation enhancer with a molecular weight of less than 1000 daltons with a plurality of nucleic acid fragments and a ligase in a ligation buffer; and permitting ligation wherein the efficiency of ligation is enhanced by at least 25% compared to the efficiency of a ligation in the absence of the small molecule enhancer.

Various embodiments include one or more of the following features:

ligation is intramolecular;

ligation is intermolecular;

the plurality of nucleic acid fragments are double-stranded DNA with blunt ends, single-base overhangs or staggered ends; and/or the efficiency of ligation is enhanced by at least 4-fold as determined by electroporation of host cell.

In general in a fourth aspect, a composition is provided that includes 0.01-200 units/µl restriction endonuclease, 0.01-2000 units/µl ligase, 0.01-200 units/µl polynucleotide kinase (PNK), in a buffer containing one or more small molecule ligation enhancers with a molecular weight of less than 1000 daltons and optionally PEG 5000-10,000.

Various embodiments include one or more of the following features:

the ligase is T4 ligase;

the one or more small molecule ligation enhancers comprise 1,2-PrD; and/or the one or more small molecule ligation enhancers are 1,2-PrD and glycerol.

In general in a fifth aspect, a method is provided for creating a polynucleotide library that includes: adding 0.01-200 units/µl restriction endonuclease, 0.01-2000 units/µl ligase, and 0.01-200 units/µl PNK in a buffer containing one or more small molecule ligation enhancers and optionally PEG 5000-10,000 to a polynucleotide amplification product; and allowing intramolecular ligation to occur for transforming competent host cells.

An embodiment includes transforming competent cells using electroporation.

BRIEF DESCRIPTION OF THE DRAWINGS

FIG. 1A shows the product of ligation in the absence of 1,2-PrD.

FIG. 1B shows the product of ligation in the presence of 4% 1,2-PrD.

FIG. 1C shows the product of ligation in the presence of 6% 1,2-PrD.

FIG. 3A shows the expected product of ligation of a linearized plasmid with single-base 3' overhangs into a circularized vector.

FIG. 3B shows the circularized product of ligation of two fragments with a single-base overhang obtained by cleaving a vector. This is a model system for "insert vector" cloning where the two fragments, each with single-base 3' overhang, are ligated into a circle.

FIG. 3C shows the circularized product of ligation of three fragments with single-base 5' overhangs. Only ligated constructs with all three pieces present and in the correct orientation lead to a viable transformant and a subsequent colony on an agar ampicillin selection plate. Assembly of just two fragments does not reconstitute the β lactamase ampicillin resistance gene, and thus does not create ampicillin-resistant colonies.

FIG. 4A refers to AhdI-pUC19 (see FIG. 3A).

FIG. 4B refers to BciVI-pUC19 (see FIG. 3B).

FIG. 4C refers to BccI-pUC19 (see FIG. 3C).

DETAILED DESCRIPTION OF THE EMBODIMENTS

Figure 1:
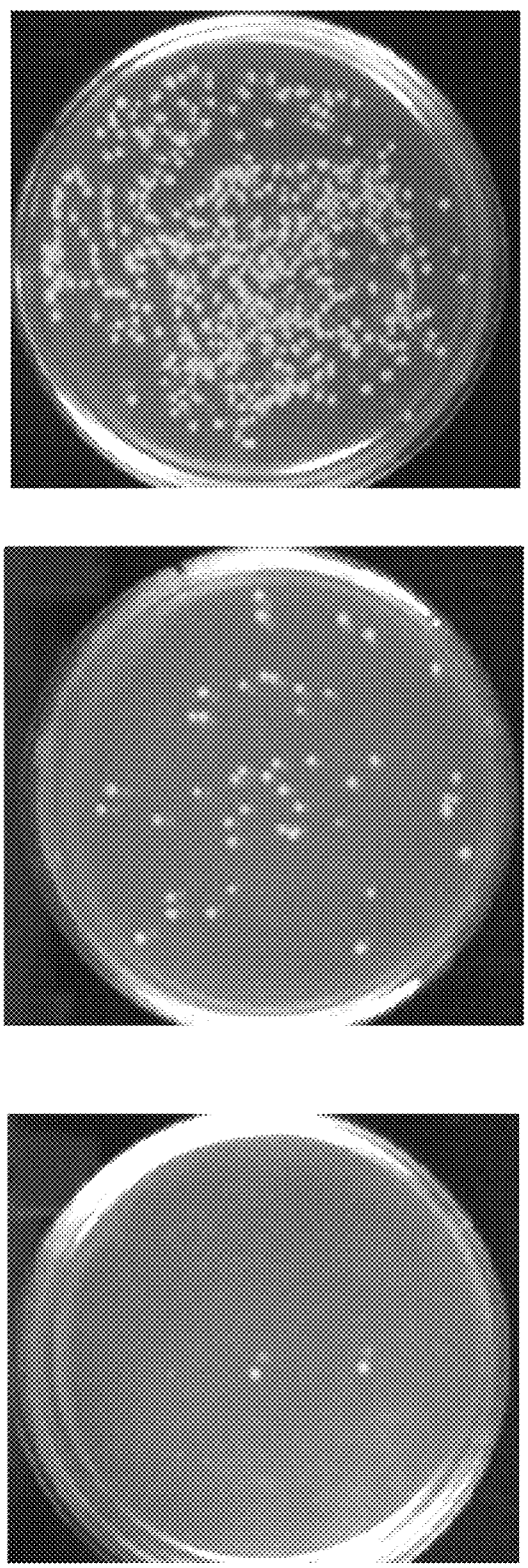
FIGS. 1A-C show the results of recircularization through ligation of double-stranded linearized plasmid DNA in the presence of increasing amounts of 1,2-PrD. The ligated DNA is subsequently transformed into competent E. coli cells, followed by plating on agar ampicillin selection plates. The extent of successful transformation is illustrated by the numbers of colonies on the plate. The greater the 1,2-PrD concentration, the greater the number of transformants.
Figure 2:
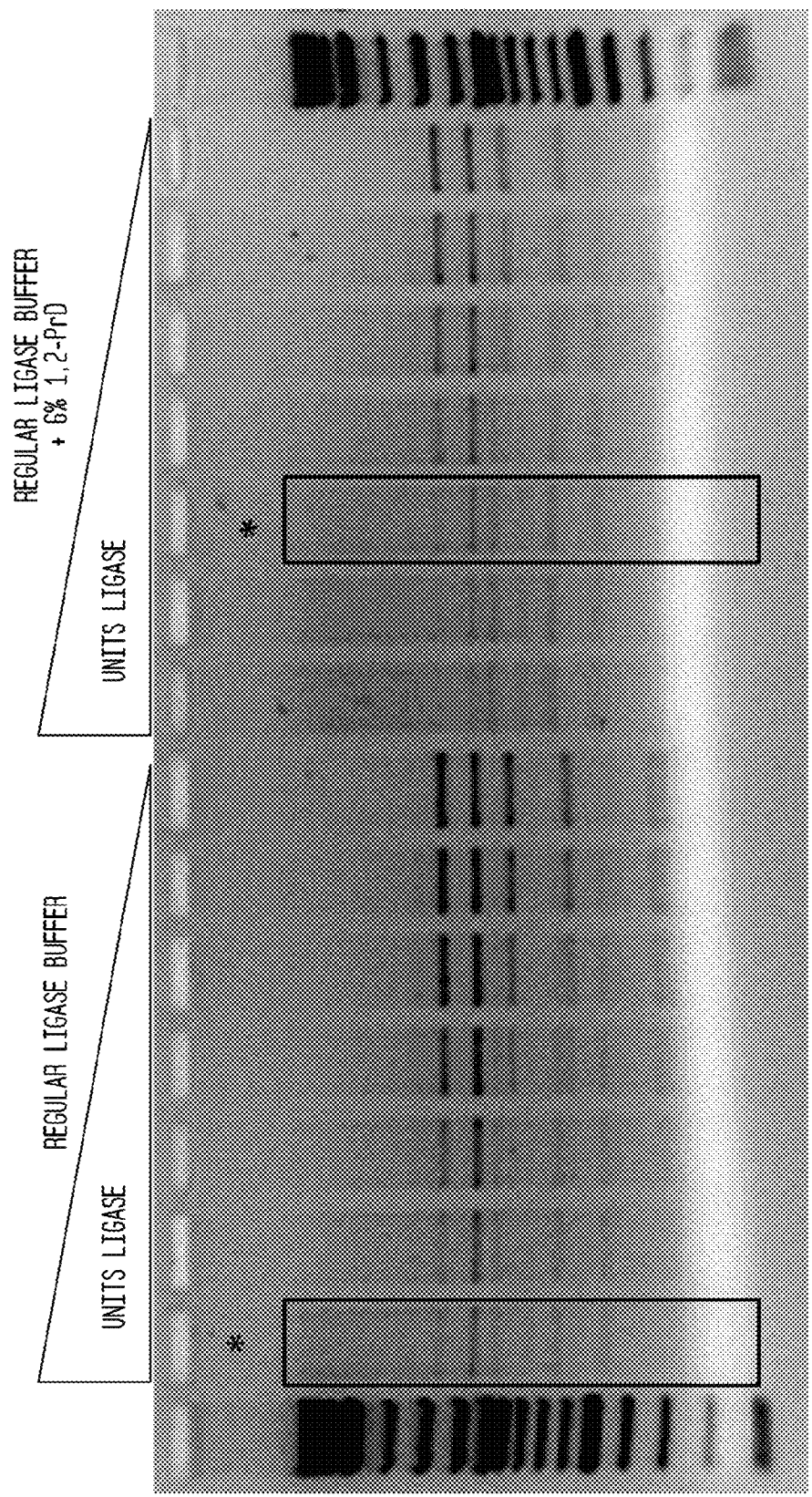
FIG. 2 shows the results of a ligase activity titer assay using blunt-ended DNA fragments which were the HaeIII restriction endonuclease cleavage products of PhiX-174 genomic DNA. The ligase activity in the absence and presence of 6% 1,2-PrD was determined in a two-fold ligase dilution series. The symbol "*" denotes equivalent levels of ligation, showing that ligation efficiency was enhanced 4-fold. The first and last lanes contain DNA markers.

In embodiments of the invention, small molecules having a molecular weight of less than 1000 daltons, 900 daltons, 800 daltons, 700 daltons, 600 daltons, 500 daltons or 400 daltons have been identified that serve as ligation enhancers. Examples of small molecule enhancers include straight or branched diol or polyol containing 2 to 20 carbons.

Examples include optionally substituted straight or branched alkylene glycols, pentaerythritol, sorbitol, diethylene glycol, dipropylene glycol, neopentyl glycol, such as propylene glycol and ethylene glycol ethers, such as 1,2-ethylene glycol, 1,2-PrD, 1,3-PrD, 1,4-butanediol, 1,5-pentanediol, 1,6-hexanediol, 2-methyl-1,3-propanediol, 2,2'-dimethylpropylene glycol, 1,3-butylethylpropanediol, methyl propanediol, methyl pentanediols, propylene glycol methyl ether, propylene glycol ethyl ether, propylene glycol butyl ether, diethylene glycol phenyl ether, propylene glycol phenol ether, propylene glycol methyl ether, tripropylene glycol methyl ether, propylene glycol isobutyl ether, ethylene glycol methyl ether, or mixtures thereof.

Additional examples of small molecule ligation enhancers include alcohols which may be substituted straight or branched and include primary, secondary, tertiary alcohol chain alkylene group or polyvalent branched chain alkyl group containing 2 to 20 carbons such as methanol, ethanol, n-propanol, isopropanol, n-butanol, n-pentanol, i- or neopentanol, n-hexanol, n-heptanol, n-octanol, 2-ethylhexanol, n-nonanol and mixtures thereof.

Additional examples of small molecule enhancers include zwitterionic compounds which are optionally substituted straight or branched and contain 2 to 50 carbons and comprise an ammonium, phosphonium or sulfonium cationic group and carboxylate, phosphate, or a sulfate group such as sulpho- or carboxy-betaines, amino acids, aminosulfonic acids, and alkaloids.

Additional examples include a polar aprotic molecule selected from the group consisting of N-alkylcaprolactams, dimethylcaprylic/capric amides, N-alkylpyrrolidons, diphenyl sulfone, DMSO, DMI, acetonitrile, acetone, diglyme, tetraglyme, THF, dimethylacetamide, and DMF.

One or more of the above-described small molecule enhancers can be added to a preparation of polynucleotides and one or a plurality of ligases to enhance ligation.

The small molecule enhancers are useful for facilitating ligation of double-stranded nucleic acids that have single nucleotide extensions or have blunt ends. The enhancers may also be used to enhance any type of ligation including those involving double-stranded nucleic acids containing 2-6 bases or even longer extensions or single-stranded nucleic acid ligation. The term "nucleic acid" as used herein refers to double-stranded DNA, double-stranded RNA and double-stranded DNA/RNA molecules in which one strand is DNA and the other is RNA or part of the molecule is double-stranded DNA and part is double-stranded RNA, or single-stranded DNA or RNA.

The term "ligase" as used herein refers to an enzyme that is commonly used to join polynucleotides together or to join the ends of a single polynucleotide. Ligases include ATP-dependent double-strand polynucleotide ligases, $NAD^+$-dependent double-strand DNA or RNA ligases and single-strand polynucleotide ligases. Present embodiments describe enhancement of ligation where the ligase is selected from any of the ligases described in EC 6.5.1.1 (ATP-dependent ligases), EC 6.5.1.2 ($NAD^+$-dependent ligases), EC 6.5.1.3 (RNA ligases) (see ExPASy Bioinformatics Resource Portal having a URL of enzyme.expasy.org which is a repository of information concerning nomenclature of enzymes based on the recommendations of the Nomenclature Committee of the International Union of Biochemistry and Molecular Biology (IUBMB) describing each type of characterized enzyme for which an EC (Enzyme Commission) number has been provided. Specific examples of ligases include bacterial ligases such as *E. coli* DNA ligase and Taq DNA ligase, Ampligase® thermostable DNA ligase (Epicentre® Technologies Corp., part of Illumina®, Madison, Wis.) and phage ligases such as T3 DNA ligase, T4 DNA ligase and T7 DNA ligase and mutants thereof. Examples of mutants include fusion ligases containing a DNA-binding domain and a ligase. Examples of fusion ligases include: Sso7-T3 DNA ligase, Sso7-T4 DNA ligase, Sso7-T7 DNA ligase, Sso7-Taq DNA ligase, Sso7-*E. coli* DNA ligase and Sso7-Ampligase DNA ligase. Other mutants may contain a mutation in the catalytic domain of the ligase that permits ligation of adenylated DNA only, such as a mutation of the lysine therein. One example is a mutation of lysine at position 159 to any other amino acid in T4 DNA ligase (Accession number of NP_049813 at NCBI). Other examples include T4 RNA ligase 1 and T4 RNA ligase 2 and mutants thereof, for example, Sso7 fusion proteins, T4 truncated and mutated (K227Q) RNA ligase.

Advantages of any of the small molecule enhancers added to one or more of the ligases described herein for joining two or more polynucleotides can be ascertained using the assays described in the examples or any of the ligase assays known in the art, for example, ligase assays described in the New England Biolabs (Ipswich, Mass.) catalogue 2011/12 on pages 172-173 and 108-110. Such assays include: inserting a DNA containing a marker (such as antibiotic resistance) into a vector and cloning the product so as to detect the presence of the marker; and assembling 2 or 3 or more nucleic acid fragments and introducing the ligation product into a host cell by transformation to determine expression of a phenotype encoded by the ligated polynucleotide.

Figure 5:
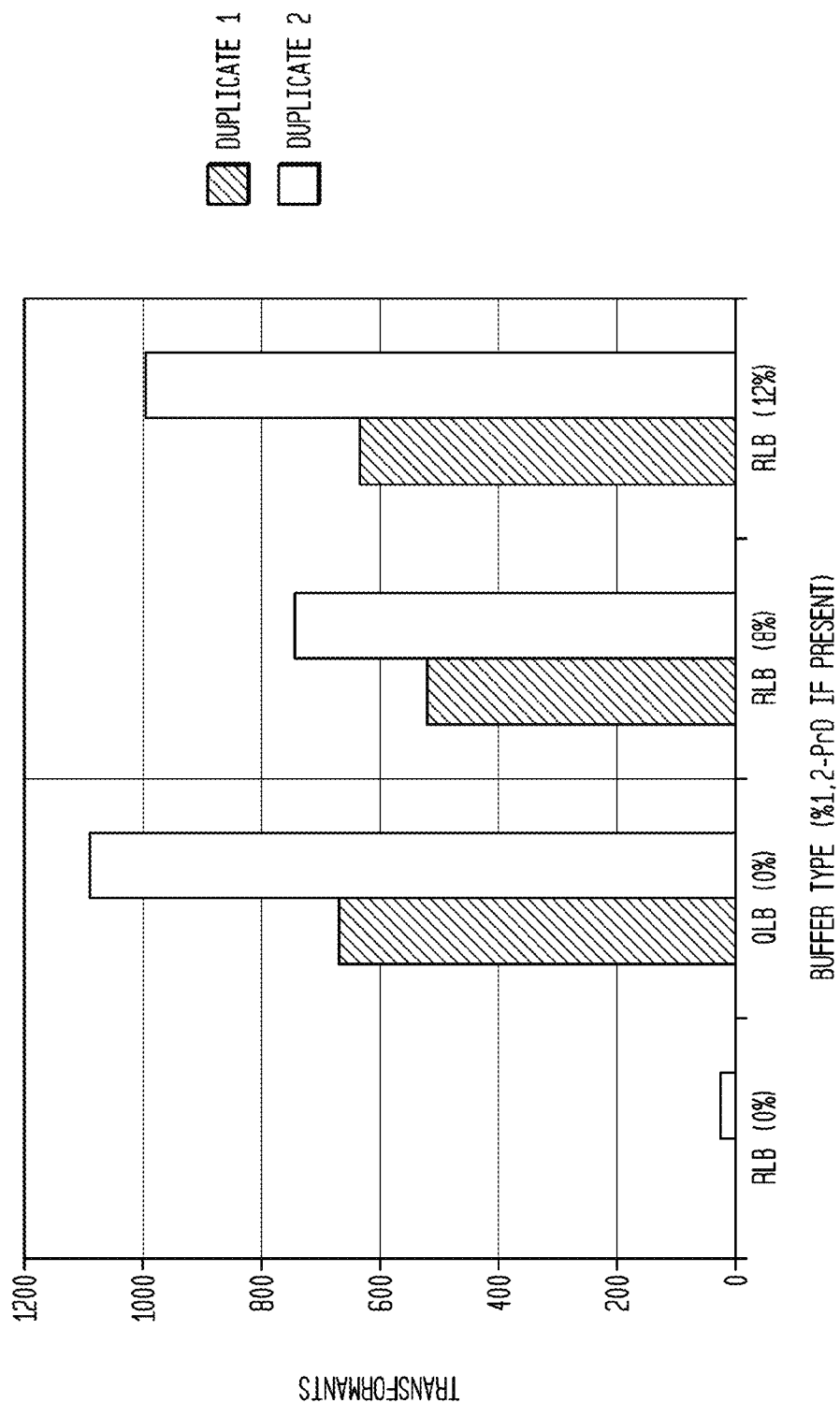
FIG. 5 shows a histogram comparing DNA ligation (and subsequent transformation of E. coli) using regular ligation buffer with varying amounts of 1,2-PrD, without 1,2-PrD and with Quick Ligase™ buffer containing PEG (NEB, Ipswich, Mass.). The addition of 1,2-PrD to the ligation buffer enhanced DNA ligation at least as much as PEG containing Quick Ligase. The Y-axis is transformants per 10 pg DNA (transformations w/chemically competent cells.) The X-axis is regular ligase buffer (RLB) with the percentage of added 1,2-PrD given in parentheses. The quick ligase buffer (QLB) has PEG in it to enhance ligation.

In some circumstances, a person of ordinary skill in the art might use a ligation buffer additionally containing PEG to facilitate difficult ligations. Unfortunately, PEG interferes with electroporation and has to be removed prior to this step. FIG. 5 shows how difficult ligations may be achieved in the presence of a small molecule enhancer in the absence of PEG. This is beneficial not only because the efficiency of ligation is enhanced but also because it avoids the need to purify the DNA away from the PEG prior to electroporation.

In embodiments of the invention, for any ligation reaction, the enhancer may be added to the ligation buffer at a concentration in the range of 1%-50% v/v, 2%-50% v/v, 3%-50% v/v, 4%-50% v/v, 5%-50% v/v, 1%-45% v/v, 1%-40% v/v, 1%-35% v/v, 1%-30% v/v, 1%-25% v/v, 1%-25% v/v, 1%-15% v/v with 0.01-2000 units/µl ligase, for example, 1-1000 units/µl ligase or 4-200 units/µl ligase. When PEG is present in the ligase buffer, a two-fold reduction in the small molecule enhancer concentration over that used in the absence of PEG can be used to further enhance ligation over that seen with PEG alone; for example, where a small molecule enhancer might be used in a range of 10%-18% v/v in the absence of PEG, 5%-9% v/v small molecule enhancer can be used with PEG. In one embodiment, blunt-end double-stranded nucleic acid ligation utilizes a small molecule enhancer at about 4% v/v in the absence of PEG. Other enzymes may be included in the ligase reaction mixture such as a restriction endonuclease such as DpnI, or a PNK such as T4 PNK where either enzyme may be added at a concentration in the range of 0.01-200 units/µl, for example 0.05-50 units/µl. In one example of a ligation reaction, a mixture of nucleic acid fragments that includes a vector and an insert in the form of separate nucleic acids can give rise to a desired ligation product in the presence of small molecule enhancers. In particular, the concentration of the enhancer is selected to favor circularization over concatamerization both for a single species of molecule and for mixtures of nucleic acids such as vector and insert combinations. It is possible to enhance the desired ligation reaction by at least 25% where for example the overall range of enhancement is at least 1.25-fold to 75-fold for example, at least 2-fold, 3-fold, 4-fold, 5-fold, 6-fold, 7-fold, 8-fold, 9-fold or 10-fold or more for molecules with single-base overhangs and by at least 25% for example at least 1.25-fold, 2-fold, 3-fold, 4-fold for blunt-ended molecules with or without PEG.

Table 1 lists small molecule enhancers of ligation. All were tested side-by-side using two ligation test systems which were: (a) cloning of a 500 bp amplicon made by Taq DNA polymerase into a T-tailed vector; and (b) recircularization of an AhdI-linearized plasmid. Both ligation test systems used DNA with single-base overhangs.

TABLE 1

| Small Molecule Enhancer | Cloning Enhancement | Recircularization Enhancement |
|---|---|---|
| No addition | 1-fold | 1-fold |
| 1,2-PrD (12%) | 14-fold | 11-fold |
| 1,3-PrD (12%) | 7-fold | 9 fold |
| Ethylene glycol (12%) | 10-fold | 8-fold |
| DMSO (6%) | 12-fold | 9-fold |
| Ethanol (12%) | 25-fold | 9-fold |
| Isopropanol (12%) | 16-fold | 10-fold |
| Betaine (1.3M) | 12-fold | 13-fold |
| Glycerol (12%) | 4-fold | 5-fold |

Table 2 shows enhancement of ligation by 6% 1,2-PrD and subsequent transformation whether the insert being cloned is a synthetic cassette made by annealing oligonucleotides or is a PCR amplicon. This test used a commercially available cloning vector from Qiagen, Valencia, Calif. (#231124) specifically designed to clone DNA fragments with single-base 3'A overhangs.

TABLE 2

| Insert | Cloning Enhancement (chemical transformation) | Cloning Enhancement (electroporation) |
|---|---|---|
| 68mer cassette featuring No 5' PO$_4$, 3' A overhang | 14-fold | 2-fold |
| 513 pb human genomic amplicon using Taq DNA polymerase | At least 72-fold (0 colonies vs. 72 colonies) | 11-fold |

The enhancement of ligation of double stranded or single stranded polynucleotides has been shown here to be compatible with other reactions which may be desirably conducted in a single tube. For example, site directed mutagenesis as described in Example 7 below, permits at least three different enzyme reactions (a restriction endonuclease, a ligase and a PNK) to occur in a single reaction tube.

Figure 6:
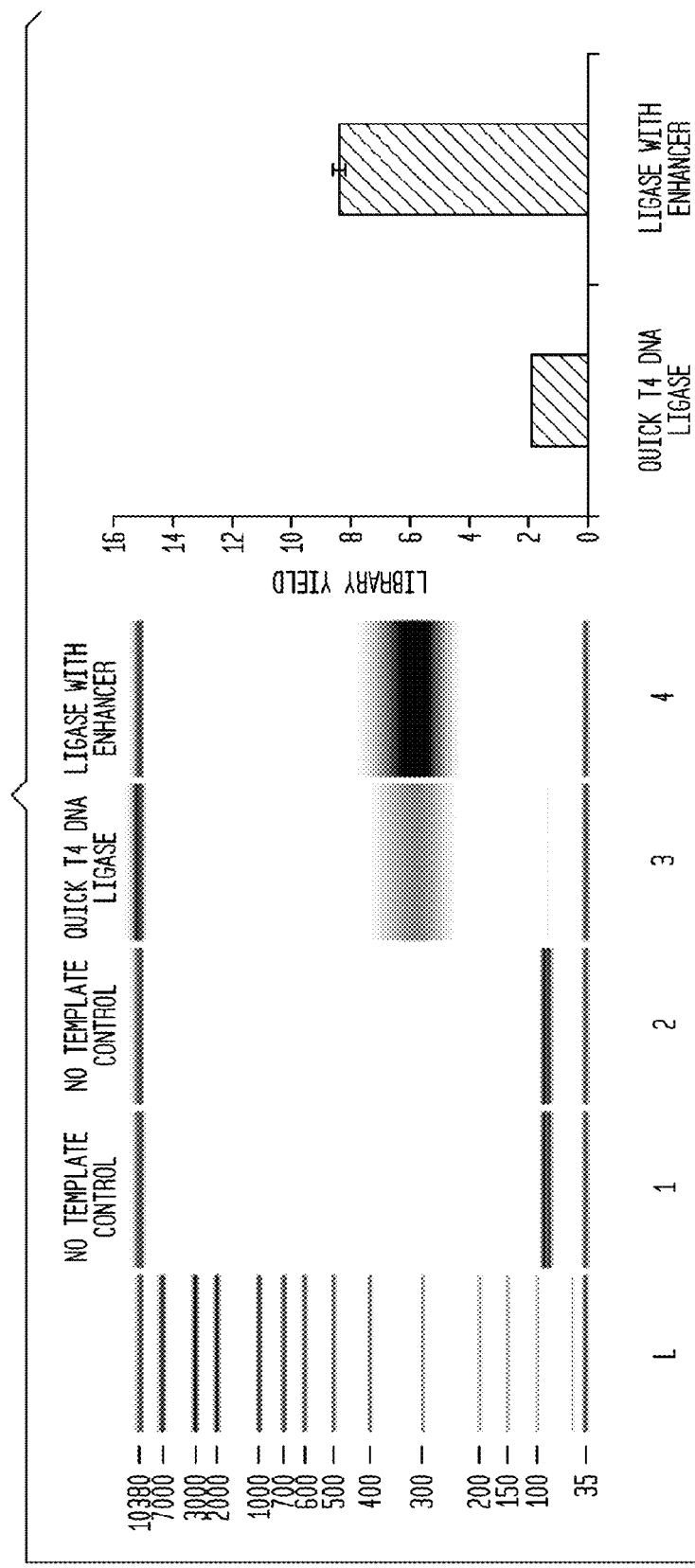
FIG. 6 shows enhanced ligation efficiency of T4 DNA ligase by a small molecule enhancer for Next Generation Sequencing (NGS) library preparation. Libraries were prepared using either T4 DNA ligase in a ligase buffer containing PEG (Quick Ligase buffer, NEB, Ipswich, Mass.) or T4 DNA ligase in a ligase buffer containing a small molecule enhancer (ligation buffer, NEB, Ipswich, Mass.) using 5 ng *E. coli* genomic DNA fragmented to 200 bp. "No template" control contained all the reagents except for DNA, and went through the whole workflow. Library yields were increased at least about 5-fold in the presence of the small ligase enhancer.

Small molecule ligase enhancers enable the development of a fast library preparation protocol with low nanogram polynucleotide input for multiple Next Generation Sequencing (NGS) platforms. Major improvements include: increased ligation efficiency of a ligase by one or more small molecule enhancers; and tolerance of a ligase to dATP inhibition in the presence of these small molecules. FIG. 6 shows the beneficial effects of small molecule ligation enhancers on T4 DNA ligase. Another application is the use of long hairpin adaptors which are normally challenging to ligate to polynucleotide fragments using a ligase. These are readily ligated to the polynucleotide fragments in the presence of small molecule enhancers with increased ligation efficiency.

All references cited herein are incorporated by reference.

EXAMPLES

Example 1

Ligation Efficiency Assay

A. Ligation Reactions

The reaction mixtures contained DNA at 50-100 ng and 1,2-PrD at different concentrations. 1 µl of regular concentration (NEB, Ipswich, Mass., #M0202; 400 units) or 1 µl of high concentration T4 DNA ligase (NEB, Ipswich, Mass., #M0202; 2000 units) was then added to a final volume of 21 µl in 1×T4 DNA Ligase Buffer (NEB, Ipwich, Mass., #B0202) or 1× Quick Ligase™ Buffer (NEB, Ipswich, Mass., #B2200).

A standard assay uses 100 ng DNA, 1 µl of T4 DNA ligase, 21 µl 1×T4 DNA ligase buffer and varying amounts of enhancer. However, we have also tested and compared (a) various concentrations and types of DNA ligase, and (b) various ligation buffers (specifically, regular and Quick Ligase) and found consistent enhancement of ligation at 1%-12% 1,2-PrD.

Ligation reactions were incubated for 10 min at room temperature (25° C.) unless otherwise stated, then placed on ice for 2 min. In some experiments the ligase was heat-killed by incubation at 65° C. for 20 min. The ligation reactions were analyzed by 1% agarose gel electrophoresis to identify DNA species and determine the efficiency of transformation.

B. Efficiency of Transformation Determinations

A volume of 2 µl from each ligation reaction was incubated with 50 µl of chemically competent (NEB, Ipswich, Mass., #C2987I) or electrocompetent (NEB, Ipswich, Mass., #C2989K) DH5 alpha E. coli cells.

For chemically competent cell transformations, the cell-DNA mixture was incubated on ice for 30 min, heat-shocked at 42° C. for 30 sec, then returned to ice for 5 min. A volume of 950 µl SOC medium (2% vegetable peptone or Tryptone, 0.5% yeast extract, 10 mM NaCl, 2.5 mM KCl, 10 mM MgCl$_2$, 10 mM MgSO$_4$ and 20 mM glucose) was added to the cell-DNA mixture, followed by a one hr 37° C. outgrowth period with agitation. A volume of 25-50 µl of appropriately diluted cells in SOC was spread onto Rich Agar plates (composition per liter: 10 g soy peptone, 5 g yeast extract, 10 g NaCl, 1 g MgCl$_2$-6H$_2$O, 1 g dextrose, 15 grams agar) supplemented with 100 µg/ml ampicillin. Plates were inverted and incubated for 16 hrs at 37° C., followed by quantification of total colony numbers.

For electrocompetent cell transformation protocols, the cell-DNA mixture was subjected to electroporation, immediately followed by the addition of 950 μl of pre-warmed 37° C. SOC medium, followed by a one hour 37° C. outgrowth period with agitation. Dilution, plating, incubation and colony quantification were performed as described in Example 1A above.

The number of colonies per ligation condition correlated with the formation of circularized DNA constructs during the ligation reaction.

Example 2

Enhanced Ligation of DNA with a Single-Base Overhang

Figure 3:
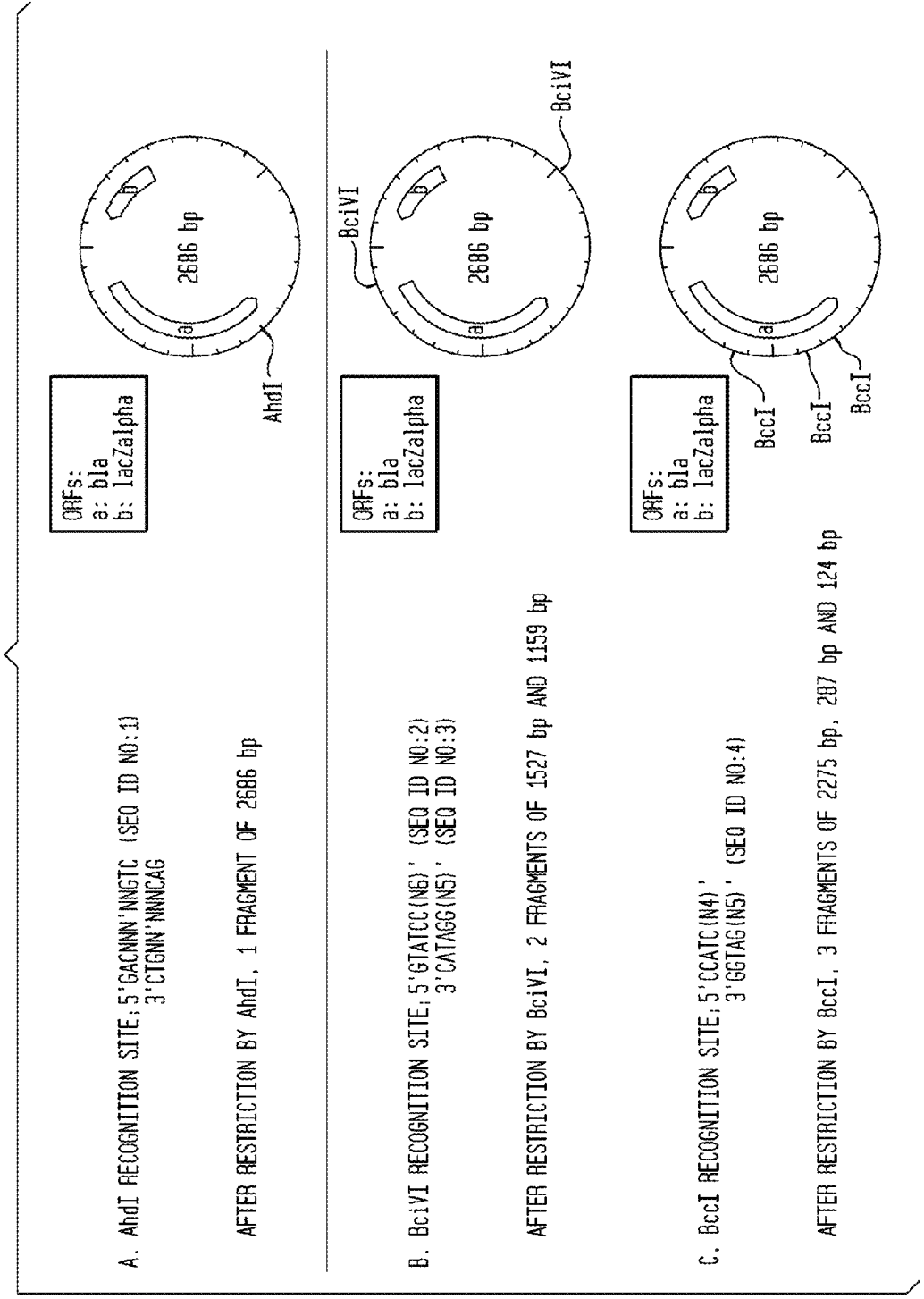
FIGS. 3A-C show how cleavage of pUC19 plasmid with the specified restriction enzyme (AhdI, BciVI and BccI) generates one, two and three fragments which when ligated properly form a circularized plasmid. Recognition sequences for AhdI (SEQ ID NO:1—top and bottom strands), BciVI (SEQ ID NOS: 2 and 3—top and bottom strands) and BccI (SEQ ID NO:4—bottom strand) are shown.

Linearization of the pUC19 plasmid was achieved using AhdI to generate single-base overhangs as described in FIG. 3A. Ligation of the cleaved DNA was performed in a 20 μl ligation reaction containing 100 ng of DNA in the presence and absence of 1,2-PrD and 400 U of T4 DNA ligase was incubated for 20 min at 16° C., then heated to 65° C. for 45 min to inactivate the ligase. Transformation of cells with the ligated DNA was performed using chemically competent NEB Turbo™ cells (NEB, Ipswich, Mass., #C2984H) as described in Example 1 using 2 μl of the ligation mix (containing 10 ng DNA) with an outgrowth period of 20 min. The results were that 1,2-PrD increased transformation levels (see FIGS. 1A-C).

Example 3

Enhanced Ligation of DNA with Blunt Ends

The effectiveness of the ligation enhancer was also established for blunt-ended DNA as follows: 20 μl reactions were set up containing two-fold serial dilutions of 2000 units of T4 DNA ligase, 200 ng PhiX174-HaeIII digest (NEB, Ipswich, Mass., #N3026), and regular ligase buffer with 200 ng phiX174-HaeIII blunt-ended fragments per 20 μl, in the absence and presence of 6% 1,2-PrD. The reactions were incubated for 30 min at room temperature (25° C.) followed by electrophoresis on a 1% agarose gel. 1,2-PrD enhanced T4 DNA ligase activity 4-fold in this titer reaction.

Example 4

No Enhancement with 1,2-PrD Alone as Determined by Mock Ligation Reactions with Supercoiled DNA Mock DNA ligations were set up with 1 ng of supercoiled pUC19 DNA in 1× regular DNA ligase buffer in the presence and absence of 2000 units T4 DNA ligase and with or without 12% 1,2-PrD. Ligation reactions were conducted using the standard protocol in Example 1 and transformations with chemically competent DH5 alpha E. coli cells. 40 μl of a 1:20 dilution of the 1 ml SOC outgrowth containing 2 pg supercoiled DNA was plated onto agarose plates and incubated overnight. The number of transformants was not statistically altered by the presence of 1,2-PrD, whether or not the T4 DNA Ligase was present.

Table 3 shows the results of a control experiment where 1,2-PrD does not affect nor interfere with transformation using a supercoiled DNA form of the plasmid pUC19. This illustrates the enhancement is at the ligation step and not the transformation step.

TABLE 3

| T4 DNA Ligase Levels | 1,2-PrD Concentration | Transformants from 2 pg SC DNA |
| --- | --- | --- |
| None | 0% | 134 |
| None | 12% | 126 |
| 2000 U | 0% | 69, 92 (duplicate reactions) |
| 2000 U | 12% | 82, 73 (duplicate reactions) |

Example 5

Figure 4:
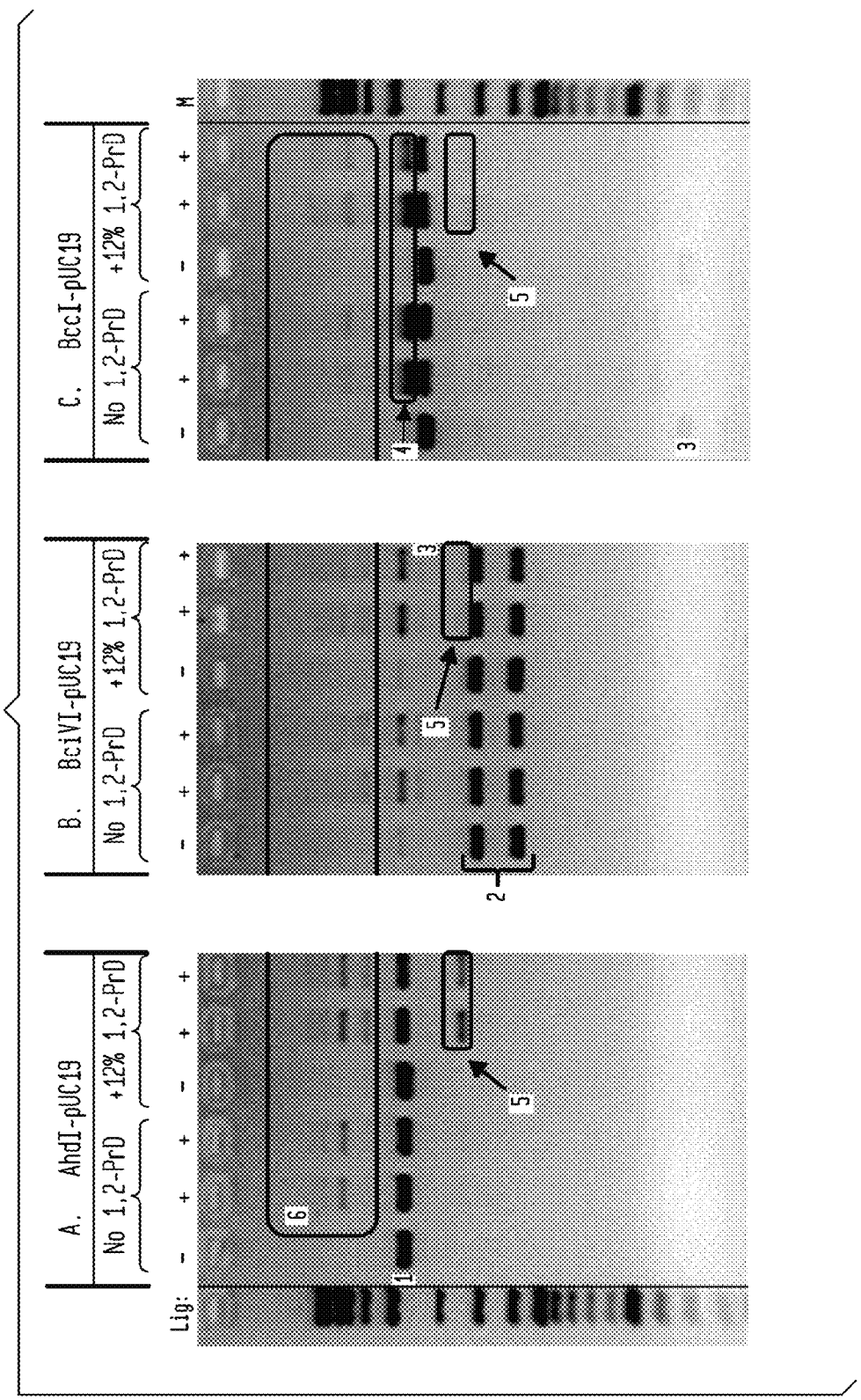
FIGS. 4A-C show agarose gel electrophoresis analysis of ligation products achieved using +/−12% 1,2-PrD for one, two and three pUC19 fragment sets as described in FIGS. 3A-C. The marker lane indicated by M corresponds to 1 µg of a 2-log DNA ladder, New England Biolabs, Inc. (NEB), Ipswich, Mass., #3200. (1) is a 2686-bp linear AhdI-pUC19 fragment; (2) are 1527-bp and 1159-bp BciVI fragments; (3) are 2 lengths (2275-bp and 287-bp) of 3 BccI fragments where the third 124-bp fragment is not visible on the gel; (4) is a linearized intermediate ligation product formed by 2275-bp and 287-bp BccI fragments; (5) is the desired ligated/circularized plasmid which is a highly transformable desired product; and (6) are different kinds of linear and circular undesired concatameric ligation products which are not highly transformable.

Enhanced Ligation Efficiency of One, Two or Three DNA Fragments into a Linearized Vector and Recircularization Single fragment ligation (recircularization), two fragment ligation (cloning) and three fragment ligation (assembly) reactions were performed in the presence of 1,2-PrD (see FIGS. 3A-C). Restriction digests of pUC19 plasmid constructs were performed to completion by monitoring the reactions using 1% agarose gel electrophoresis. Upon completion all restriction enzymes were heat-inactivated by incubating the reaction for 20 min at 65° C. The DNA was purified by use of QiaQuick® (Qiagen, Valencia, Calif.) spin columns and quantified by comparison to known DNA standards by 1% agarose gel electrophoresis. The gel electrophoresis analysis shown in FIGS. 4A-C showed the products made with single (linearized), two and three fragment ligation reactions using restricted pUC19 plasmid DNA. Ligation reactions were performed as described in FIGS. 3A-C using 100 ng of DNA that had been restricted by AhdI, BciVI or BccI to leave a variety of single-base overhangs. From each 21 μl ligation reaction, 2 μl was used for transformation as analyzed in Table 4 and 19 μl was run on a 1% agarose gel prepared with tris-borate as described in FIGS. 4A-C. These figures show that 1,2-PrD had a significant beneficial effect on the amount of ligated circularized plasmid as indicated by arrow 5 for each plasmid test system. This is the highly transformable DNA circularized form.

Table 4 below shows the results of ligations performed on the constructs described in FIGS. 3A-C as described in the basic protocols using 1×T4 DNA Ligase Buffer and 100 ng of pUC19 DNA that had been restricted as listed in column 1 (and diagrammed in FIGS. 3A-C), purified with QiaQuick® spin columns and quantified against known DNA standards (lambda-HindIII fragments). The ligations took place with and without 12% 1,2-PrD present for 10 min at room temperature (25° C.) with 2000 units T4 DNA ligase. A volume of 2 μl from each ligation reaction was transformed into chemically competent DH5 alpha cells as described in Example 1. A volume of 40 μl of a 1:20 dilution of the outgrowth in SOC medium was plated on medium Rich Agar plates supplemented with ampicillin. This volume corresponded to 20 pg of DNA from the original ligation reaction.

TABLE 4

| DNA Fragments Used for Ligations | Nucleotide Identity at the Single Base Overhang | Resultant Colonies (Transformation Efficiency) −1,2-PrD | Resultant Colonies (Transformation Efficiency) +1,2-PrD | Ligation/ Subsequent Transformation Enhancement |
|---|---|---|---|---|
| 1 fragment (AhdI-linearized pUC19) | 3'-C, 3'-G | 84 (4.2 × 10e$^6$/μg DNA) | 1027 (51.4 × 10e$^6$/μg DNA) | 12-fold |
| 2 fragments (BciVI-pUC19 | 3'-C, 3'-G 3'-A, 3'-T | 0 | 35 (1.8 × 10e$^6$/μg DNA) | At least 35-fold |
| 3 fragments (BccI-pUC19) | 5'-C, 5'-G 5'-C, 5'-G 5'-A, 5'-T | 2 (1.0 × 10e$^5$/μg DNA) | 37 (1.85 × 10e$^6$/μg DNA) | 18-fold |

Example 6

Comparison of the Numbers of Transformants Achieved in the Presence or Absence of 1,2-PrD in T4 DNA Ligase Buffer and Quick Ligase™ Buffer Containing PEG 6000

Ligations were performed in both buffers using 50 ng of AhdI-linearized pUC19 double-stranded DNA (containing single-base overhangs) following the conditions described in Example 1. A total of 10 pg DNA (40 μl of a 1:20 dilution of the SOC outgrowth) was used per plate and transformants were counted after 16 hrs at 37° C. FIG. 5 shows that even for the most difficult to ligate double-stranded DNA ends, 1,2-PrD in regular ligase buffer achieved the level of transformation expected or greater than in PEG-containing (quick ligase) buffers.

Example 7

Ligation of Blunt-Ended DNA and DNA with T/A Overhangs Using a Plurality of Small Molecule Enhancers Reaction conditions were utilized according to Example 1 for T4 ligase in Quick Ligase buffer, and for Taq ligase reaction buffer (NEB, Ipswich, Mass.). In addition to 5-10% PEG 6000 5%-15% glycerol and 1-8% 1,2-PrD were included in the reaction mixtures together with blunt-ended double-stranded DNA or DNA with a T/A overhang. The ligated DNA was transformed into host cells using chemically competent cells as described in Example 1. An improvement of at least 25% in efficiency of ligation was observed in multiple samples in which glycerol and 1,2-PrD were included in addition to PEG 6000 compared with ligation efficiencies in the presence of PEG 6000 only as a control. When the ligated DNA was introduced into host cells using electroporation (see Example 1), at least a 50-fold improvement was observed over the control.

Example 8

A Method for Phosphorylating and Ligating Blunt-Ended Products from a High-Fidelity Amplification Reaction Using a Multi-Enzyme Mixture A mixture of enzymes comprising 0.01-200 units/μl DpnI, 4-200 units/μl T4 ligase, 0.01-20 units/μl T4 PNK, buffer, 3-10% 1,2-PrD, 3-10% PEG 6000 and 2-20% glycerol in a ligase buffer as described above was added to the PCR amplification product obtained using non-phosphorylated promoters, unmodified end to end primers and plasmids containing a DNA of interest.

In a single-reaction tube, the PCR product was phosphorylated using T4 PNK and the ends were ligated to form a closed circle using T4 DNA ligase or Taq ligase. The parental template was cleaved with DpnI to reduce the background of undesired colonies.

The circularized product was used to transform cells. A significantly improved number of colonies of transformed host cells were obtained compared to controls absent the small molecule ligation enhancer and the ability to remove template, phosphorylate and ligate in a single step significantly enhanced the efficiency of the entire site-specific mutagenesis reaction.

What is claimed is:

1. A method of enhancing ligation between nucleic acid fragments, the method comprising:
   (a) mixing a composition comprising T4 DNA ligase and a ligase reaction buffer comprising one or more small molecule diol ligation enhancers having a molecular weight of less than 500 daltons at a concentration of 1%-50% v/v, with a plurality of nucleic acid fragments in a ligation buffer; and
   (b) permitting ligation wherein the efficiency of ligation is enhanced by at least 25% compared to the efficiency of a ligation in the absence of the small molecule enhancer.

2. A method according to claim 1, wherein ligation is intramolecular.

3. A method according to claim 1, wherein ligation is intermolecular.

4. A method according to claim 1, wherein the plurality of nucleic acid fragments are double-stranded DNA with blunt ends, single-base overhangs or staggered ends.

5. A method according to claim 1, wherein the efficiency of ligation is enhanced by at least 4-fold as determined by electroporation of host cell.

6. The method of claim 1, wherein the one or more small molecule diol ligation enhancers are selected from the group consisting of 1,2-propanediol (1,2-PrD), 1,3-propanediol (1,3-PrD), 2-methyl-1,3-propanediol, 2,2-dimethyl-1,3-propanediol, 1,3-butanediol, 1,4-butanediol, 1,5-pentanediol, 1,6-hexanediol, 1,9-nonanediol, 1,12-dodecanediol, 1,3-butylethylpropanediol, methylpropanediol, and methylpentanediols.

* * * * *